(12) United States Patent
Arslantas et al.

(10) Patent No.: US 7,780,947 B2
(45) Date of Patent: Aug. 24, 2010

(54) TAME BASED CHELATORS AND USES THEREOF

(75) Inventors: Enver Arslantas, Constance (DE); Richard R. Schmidt, Constance (DE); Peter M. Smith-Jones, New York, NY (US); Gerd Ritter, New York, NY (US)

(73) Assignees: Sloan-Kettering Institute for Cancer Research, New York, NY (US); Ludwig Institute for Cancer Research, New York, NY (US)

( * ) Notice: Subject to any disclaimer, the term of this patent is extended or adjusted under 35 U.S.C. 154(b) by 1077 days.

(21) Appl. No.: 10/582,195

(22) PCT Filed: Dec. 3, 2004

(86) PCT No.: PCT/US2004/040595

§ 371 (c)(1), (2), (4) Date: Jul. 12, 2006

(87) PCT Pub. No.: WO2005/060569

PCT Pub. Date: Jul. 7, 2005

(65) Prior Publication Data

US 2007/0148087 A1    Jun. 28, 2007

Related U.S. Application Data

(60) Provisional application No. 60/528,744, filed on Dec. 11, 2003.

(51) Int. Cl.
*A61K 51/00* (2006.01)
*A61M 36/14* (2006.01)

(52) U.S. Cl. ............... 424/1.11; 424/1.65; 424/9.36

(58) Field of Classification Search ................ 424/1.65
See application file for complete search history.

(56) References Cited

OTHER PUBLICATIONS

Enver Arslantas et al., "TAME-Hex A—A Novel Bifunctional Chelating Agent for Radioimmunoimaging," European Journal of Organic Chemistry, (19), 3979-3984 CODEN: EJOCFK; ISSN: 1434-193X, 2004.

*Primary Examiner*—Michael G Hartley
*Assistant Examiner*—Melissa Perreira
(74) *Attorney, Agent, or Firm*—Fulbright & Jaworski LLP

(57) ABSTRACT

New bifunctional chelation complexes are described. These are based on the structure of the so-called "TAME-HexA" molecule. The compounds are especially useful for forming chelation complexes with metal ions, including radioisotopes.

12 Claims, 4 Drawing Sheets

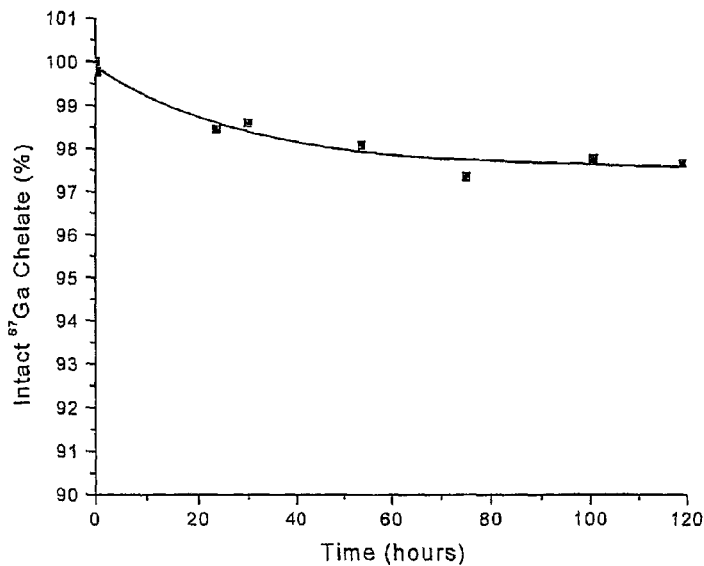
*Figure 2.* Stability of $^{67}$Ga-8 to transchelation by a 1000 fold excess of DTPA at an ambient temperature.
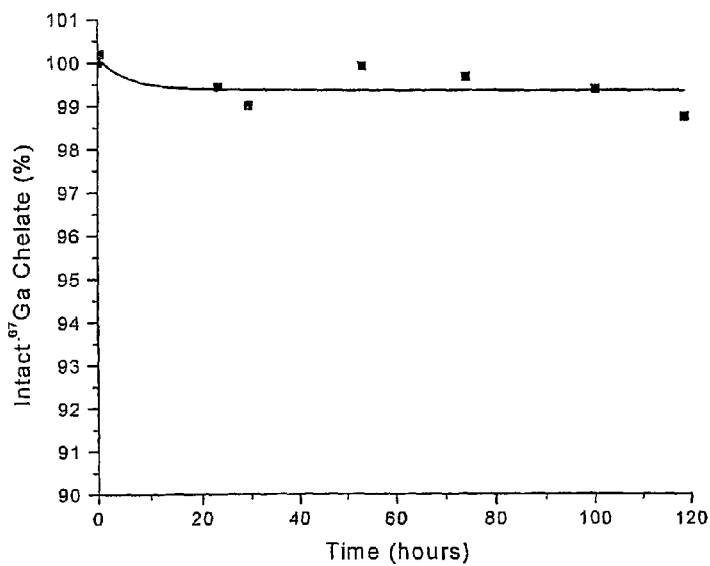
*Figure 3.* Stability of $^{67}$Ga-15 to transchelation by a 1000 fold excess of DTPA at an ambient temperature.

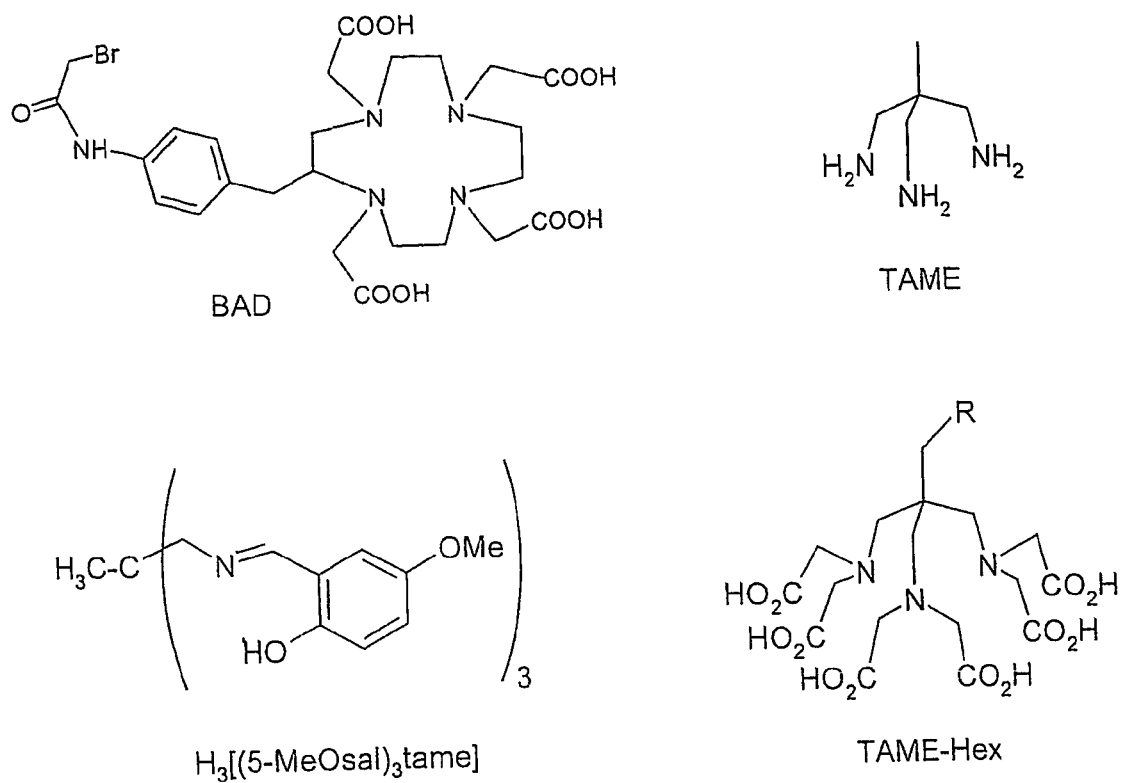
Figure 4: The structures of BAD, TAME, $H_3[(5-MeOsal)_3tame]$ and TAME-Hex

TAME BASED CHELATORS AND USES THEREOF

FIELD OF THE INVENTION

This application is a §371 of PCT/US2004/040595 filed Dec. 3, 2004 which claims priority from U.S. Provisional Application No: 60/528,744 filed Dec. 11, 2003, hereby incorporated by reference.

This invention relates to novel chelating agents, as well as their synthesis and use. The chelators can be used to form complexes with, e.g., metal ions, including heavy metal ions, which can be labelled to give a detectable signal, or otherwise give a detectable signal, such as radioisotopes. Non-radioactive metal ions, i.e., so-called "cold metal" ions, can also be chelated, to form complexes useful in, e.g., MRI work. The chelators can be used to attach these labelled moieties to molecules, such as, but not being limited to, antibodies.

BACKGROUND AND PRIOR ART

The use of bifunctional chelating agents, such as EDTA, is well known in fields such as medicinal chemistry. They are used, for example, in the diagnosis and treatment of cancer. See, e.g., Sgouros, *Encyclopedia of Cancer, Second Edition*, (Vol. 4, New York, 2002, pp. 29-40).

To elaborate on the use of these chelators in, e.g., cancer diagnosis and therapy, a chelator combines with and sequesters a therapeutic or diagnostic agent, such as a metal ion, which may be radioactive, and the combination is combined with a molecule that targets a cell, organ, etc., of interest. Examples of such molecules are antibodies of all types (e.g., polyclonal, monoclonal, chimeric, humanized, human, oligomeric, and fragmented antibodies), peptides, or ligands for receptors. For some discussion of relevant molecules, see Heppeler, et al., *Chem. Eur. J*, 5(7):1974-1981 (1999); Fu, et al., *Eur. J. Org. Chem.*, 3966-3973 (2002). When combined in this way, the agent, e.g., a radio-pharmaceutical, targets, e.g., malignant tissue, and the risk of unspecific radiation, etc., is minimized.

Ideal chelators have high thermodynamic stability paralleling their chelates, and should also be relatively inert in vivo, to reduce complications caused by loss of the chelate.

Exemplary of chelators now in use are "DTPA" (diethylenetri amninetetraacetic acid), (Brechbiel, et al., *J. Chem. Soc. Perkin Trans.*, 1:1173-1178 (1992)); and DOTA (1,4,7, 10-tetraazacyclododecane-N, N', N", N'41 -tetraacetic acid), and derivatives like "BAD", described by Kukis, et al., *Canc. Res.*, 55:878-884 (1995). There is always interest, however, in new chelators with improved properties, or different properties, useful in different applications.

The chelator "TAME," or 1,1,1-Tris-(aminomethyl) ethane, described by Geue, et al., *Aust. J. Chem.*, 36:927-935 (1983), and incorporated by reference, is known as a tridentate ligand, and as a starting material for more complex ligands, as shown by Geue, et al., supra. For example, Green, et al., *J. Am. Chem. Soc.*, 106:3689-3691 (1984) describe salicylaldimines of TAME, as chelating agents for incorporation of gallium ions, such as $Ga^{3+}$ ions. $Ga^{3+}$, when used with the positron emitting isotope $^{68}Ga$, is useful in "positron emission tomography" or "PET." The skilled artisan is very much aware of the usefulness of this technique in medical diagnosis. The chelating agent $H_3[(5-MeOsal)_3tame]$, a TAME derivative, is described by Green, et al., *J. Nucl. Med.*, 26:170-180 (1985), as being useful in assessing myocardial blood flow.

The structures of the chelators described supra are presented, in FIG. 4, for ease of reference.

While Viguier, et al., *Eur. J. Inorg. Chem.*, 2001:1789-1795, incorporated by reference, discloses monofunctional TAME-based polyaminocarboxylic acids, the art does not describe any bifunctional chelating agents, based on TAME, which would be useful for radioimmuno imaging, or therapy. Similarly, there are no reports on TAME based, polyamino polycarboxylic acids.

It is a purpose of this invention to describe the synthesis of new chelators, based upon the basic TAME structure. This chelators are tripodol, and are bifunctional or monofunctional. When complexed with metal ions, for example, radioisotopes, such as $^{67}Ga^{3+}$ and/or $^{68}Ga^{3+}$, they are useful in the diagnostic and therapeutic modalities discussed supra.

Various features of the invention are described in the description which follows.

BRIEF DESCRIPTION OF THE FIGURES

FIG. 2 shows stability studies using $^{67}Ga$ and the compound depicted by "8" in FIG. 1.

FIG. 3 shows stability studies using $^{67}Ga$ and the compound depicted by "15" in FIG. 1.

FIG. 4 shows the structures of the various known chelators discussed herein.

DETAILED DESCRIPTION OF PREFERRED EMBODIMENTS

EXAMPLE 1

Figure 1A:
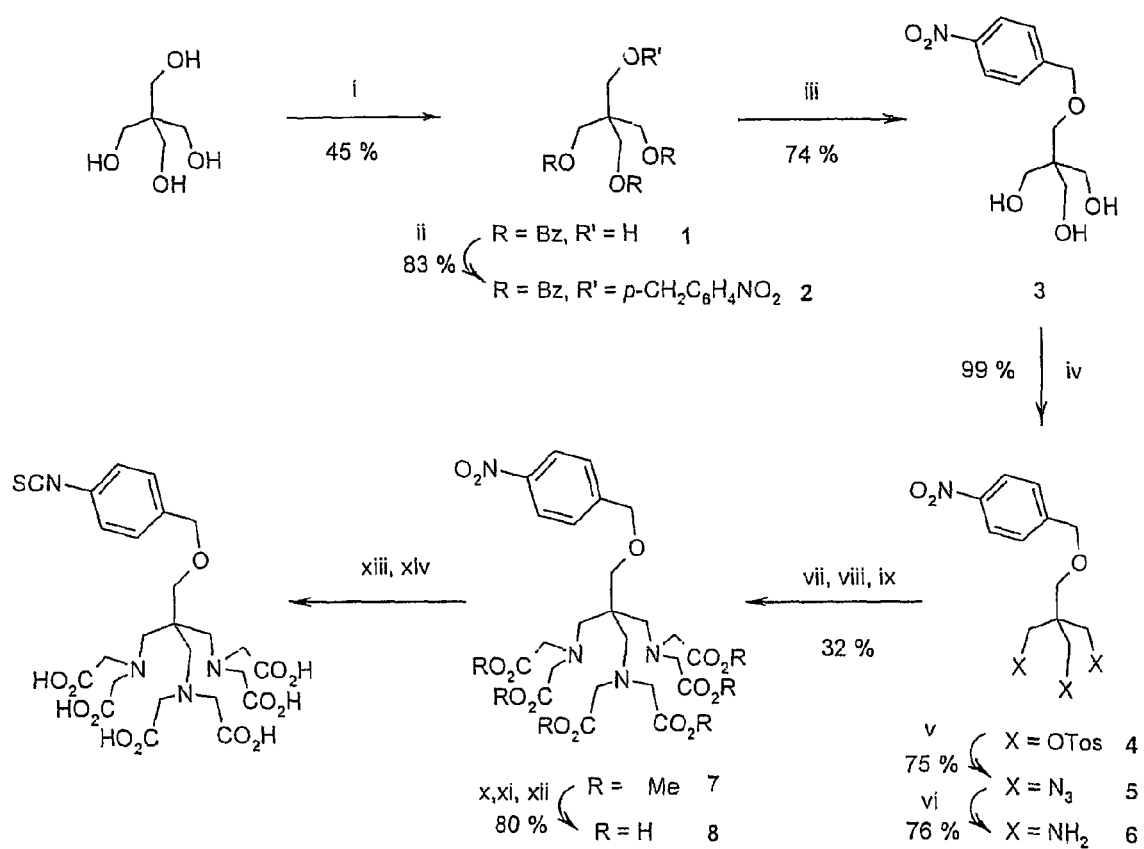
FIGS. 1a and 1b sets forth the scheme for the synthesis of the two chelators described herein. Reference is made in the examples to the numerical identifiers for each compound.

A suspension of pentaerythritol (1.3 g, 9.5 mmol), in 15 ml of dry pyridine, was stirred well, and benzoyl chloride (3.6 ml, 31 mmol), was added to it, slowly, at room temperature, with stirring. After 3 hours of stirring, 120 ml of water were added, and the mixture was extracted with 120 ml of ethyl acetate, to yield an organic layer, and an aqueous one.

The organic layer was washed with a $_5$% HCl solution (100 ml), and 100 ml of water, dried over $MgSO_4$ and evaporated. The residue was purified, via flash chromatography, on a silica column using toluene/acetone in a 10:1 ratio. A viscous, colorless oil (1.9 g) resulted (4.3 mmol, 45% yield). $^1$H-NMR data (250 MHz, $CDCl_3$) were δ=2.76 (t, 1H, $^3$J=6.8 Hz, $CH_2OH$), 3.68 (d, 2H, $^3$J=6.8 Hz, $CH_2OH$), 4.60 (s, 6H, $C(CH_2O)_3$), 7.38-8.04 (m, 15H, 3Ph). $C_{26}H_{24}O_7 \cdot H_2O$ (466.5), calc.: C 66.94, H 5.62; found: C 66.47, H 5.50.

Figure 1B:
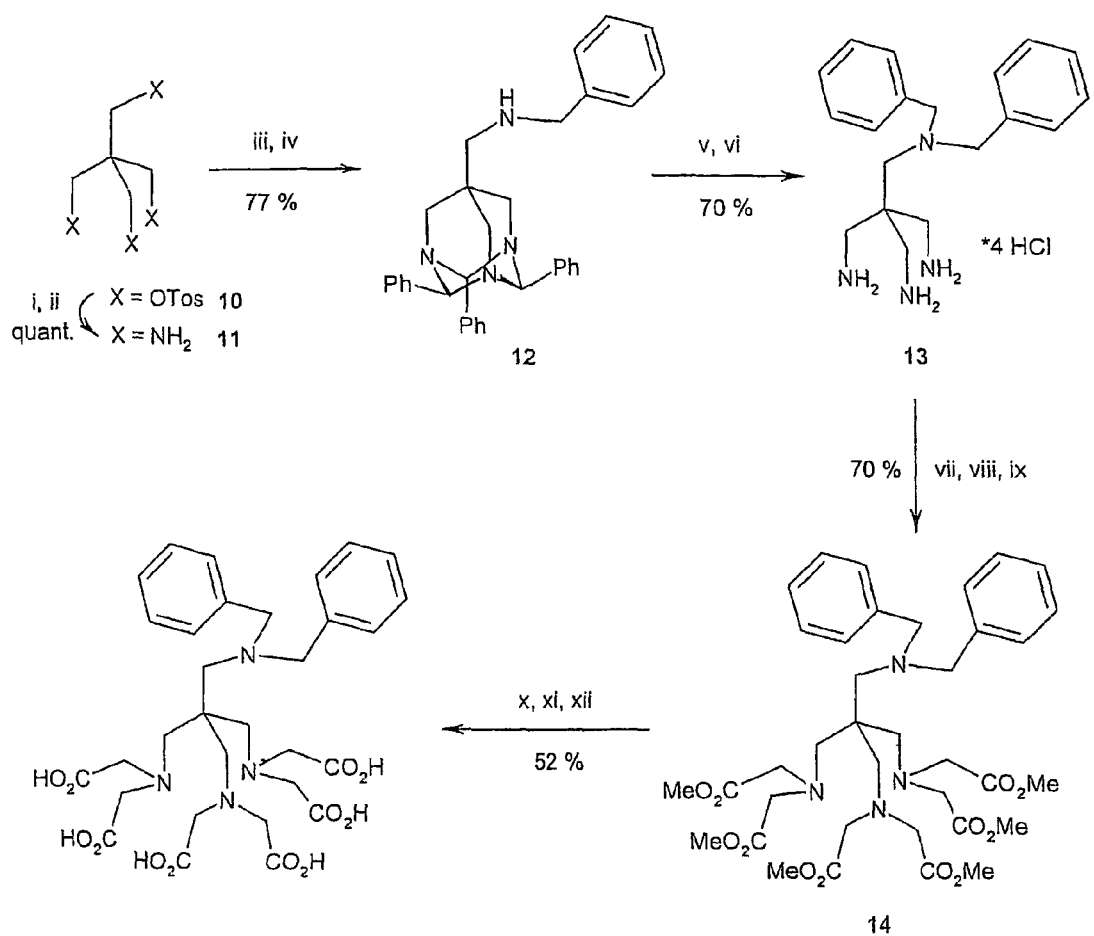

The structure of this compound, i.e., Tri-O-benzoyl pentaerythriol, is presented as "1" in FIG. 1.

This reaction involved three equivalents of benzoyl chloride for the pentaerythriol, which resulted in a product containing three benzoyl groups, which was easily isolated from over and under benzoylated compounds.

EXAMPLE 2

The Tri-O-benzoyl-pentaerythriol synthesized in the preceding example was used as a starting material to make Tri-O-benzoyl-O-(4-nitrobenzoyl)-pentaerythriol. To elaborate, 4.25 g of "1" (9.47 mmol), 3 Å molecular sieves (4.0 g), silver oxide (3.3 g, 14.2 mmol), and 4-nitrobenzoyl bromide (67 mg, 0.31 mmol), were combined in 35 ml of dry $CH_2Cl_2$, and stirred for forty hours. Following this, the mixture was filtered, and the filtrate was evaporated. Residue was applied to a silica column, and chromatographed, using $CH_2Cl_2$ as eluent. The result was 4.6 g, 7.88 mmol, 83% yield, of "2" in FIG. 1. The $^1$H-NMR data (250 MHz, $CDCl_3$), were as follows: $\delta$=3.77 (s, 2H, $CH_2OCH_2Ar$), 4.60 (s, 2H, $OCH_2Ar$), 4.64 (s, 6H, $C(CH_2O)_3$), 7.37-8.02 (m, 19H Ar, 3 Ph). $C_{33}H_{29}NO_9$ (583.6) calc.: C 67.92, H 5.01, N 2.40 found: C 67.18, H 5.04, N 2.53.

In the reaction, supra, silver (I) oxide was used rather than sodium hydride, because sodium hydride generally does not permit O-alkylation with p-nitrobenzyl bromide. See, Fukase, et al., *Tetrahedion Lett.*, 31(3):389-392 (1990).

EXAMPLE 3

The compound produced supra was acylated. The deacylation, resulting in compound "3" of FIG. 1, is described herein.

A mixture of 4.55 g (7.8 mmol) of "2" in $CH_2Cl_2$ (20 ml), MeOH (40 ml), and NaOMe (300 mg, 5.5 mmol) was prepared. The $CH_2Cl_2$ was added first, and the mixture was well stirred before the other components were added. The mixture was stirred, at room temperature for 24 hours, and then neutralized with an acidic resin, filtered and concentrated under reduced pressure. Residue was crystallized from 40 ml toluene, yielding O-(4-nitrobenzyl) pentaerythriol (1.56 g, 5.77 mmol, 74% yield), as a colorless solid. This is "3" in the figure. It had a melting point of 107° C. $^1$H-NMR (250 MHz, $CDCl_3$) are: $\delta$=2.23 (t, 3H, $^3$J=6.7 $H^2$, $CH^2OH$), 3.56 (s, 2H, $CH_2CH2Ar$), 3.75 (d, 6H, $^3$J=6.7 $H_2$, $C(CH_2OH))_3$), 4.6 (s, 2H, $OCH_2$ Ar), 7.46 (d, 2H, $^3$J=8.8 $H_2$, Ar). $C_{12}H_{12}NO_6$ (271.3). Calc.: C 53.13, H 5.32, N 5.16. Found: C 53.23, H 5.92, N 4.74. The total yield of "3" over three steps was 28%.

EXAMPLE 4

This example describes the crucial step of converting three hydroxyl groups in "3" to amine groups, as evidenced by "4" in the figure. To summarize what follows, threefold tosylation of "3," to form "4," followed by nucleophilic substitution of "4" with sodium azide in DMSO, to form 5, and reduction of this triazide to form the triamine of "6," via the Staudinger reaction, accomplished the goal. All numerical references are to FIG. 1.

To do this, 3.03 g, 11.2 mmol of "3" were dissolved in 90 ml of dry pyridine, followed by addition of 8.60 g, (45.1 nmol) of tosyl chloride, and then 140 mg, (1.15 nmol) of DMAP. This mixture was stirred for 8 hours at room temperature, and then 8 hours at 40° C. The mixture was poured into 250 ml ice water, and extracted with 250 ml $CH_2Cl_2$, resulting in organic and aqueous layers. The organic layer was washed with 250 ml of water, dried over $MgSO_4$, and concentrated. Solid residue was purified by treating it with 100 ml of warm MeOH, resulting in compound 4 (8.14 g, 11.1 mmol, 99% yield). The compound was a colorless solid, melting point 134° C. $^1$H-NMR (250 MHz, $CDCl_3$): $\delta$=2.44 (s, 9H, 3 $CH_3$ {Tos}, 3.40 (s, 2H, $CH_2OCH_2Ar$), 4.42 (s, 2H, $OCH_2$ Ar), 3.94 (s, 6H, $C9CH_2O))_3$), 7.30-8.18 (m, 16H, Ar, 3Tos). $C_{33}H_{35}NO_{12}S_3$ (733.8). calc.: C54.01, H4.94, N 1.61.

Following this synthesis, compound 4 was converted to 3-azido-2,2-bis (azidomethyl)-1-(4-nitrobenzyloxy) propane, compound "5" in the figure. This was done by forming a solution of "4" (4.96g, 6.76 nmol), in 100 ml of dry DMSO, and then adding 5.3 g, or 81 mmol of sodium azide, followed by stirring for 20 hours at 90° C. The mixture was then cooled to room temperature, and poured into 300 ml of cold water. This mixture was then extracted, with ether, in two steps (200 ml and then 100 ml). The organic layer was washed, twice, with brine, and then dried over $Na_2SO_4$. It was concentrated under reduced pressure to yield 2.03 g, (5.10 mmol, 75% yield) of compound 5, which was a yellowish oil. This could be used without further purification. 1H-NMR (250 MHz, $CDCl_3$) data are as follows: $\delta$=3.39 (s, 6H, $C(CH_2O)_3$), 3.50 (s, 2H, $CH_2OCH_2$ Ar), 4.62 (s, 2H, $OCH_2$ Ar), 7.45-8.24 (m, 4H, Ar).

The triazide was then converted to a triamine, i.e., 2-(aminoethyl)-2-[(4nitrobenzyl) oxymethyl]-propane-1,3-diamine, given as "6" in the figure, via the Staudinger reaction. To elaborate, 347 mg, or 0.87 mmol of "5" were dissolved in 5 ml of THF, and then 913 mg (3.5 mmol) of triphenylphosphine, also dissolved in 5 ml of THF, was added to the solution of "5", which was stirred, and ice cold, and was kept under an Ar atmosphere. A total of 2 ml water was added, and the mixture was stirred, at room temperature for 12 hours, followed by six additional hours; at 50° C. The solution was allowed to cool, and was then neutralized by adding concentrated HCl (0.2 ml), after which the mixture was concentrated under reduced pressure. The residue was partitioned between 40 ml of $CH_2Cl_2$ and 40 ml of 0.5 MHCl, and the aqueous phase was extracted, twice, with 30 ml of $CH_2Cl_2$ each time. The aqueous layer was rendered alkaline (i.e., a pH of 9-10), with NaOH, followed by four extractions with 30 ml of $CH_2Cl_2$ each time. The organic layer was dried over $Na_2SO_4$, and concentrated, to yield 211 mg (0.66 mmol, 76%), of the triamine of 6, as a colorless oil. This was used in the experiments which follow.

EXAMPLE 5

All of compound 6 was used in order to add carboxymethyl functionalities, forming compound 7, i.e., tetramethyl 2-[bis (methoxycarbonyl methyl) amino]-2-[(4-nitrobenzyl) (oxymethyl)]-propylene- 1,3-dinitrilotetraacetate. While direct alkylation with bromoacetic acid is possible, in theory, the isolation of the resulting, highly polar product, and monitoring the reaction progress are difficult. As a result, a bromoacetic ester is preferred.

The traimine of 6 was dissolved in 5 ml of dry DMF (211 mg, 0.66 mmol), which had been saturated with Ar. The solution was then alkylated with tert-butyl bromoacetate (0.97 ml, 6.5 mmol), and $Na_2CO_3$ (687 mg, 6.5 mmol), at 65° C., for 18 hours. The reaction mixture was stirred for 12 hours, at room temperature, and then diluted with 50 ml of ether, and 50 ml of water, to form an organic layer and an aqueous layer.

The organic layer was washed with 50 ml of brine, then dried over $Na_2SO_4$, concentrated, subjected to flash chromatography, (petroleum ether/ethyl acetate, 10:1), yielding a hexaalkylated product as a colorless oil (253 mg, 0.27 mmol, 41%). $R_f$=0.68 (petroleum ether/acetate, 4:1).

Better purification resulted, however, when this compound was converted into the hexa(methyl ester) by cleaving the tert butyl ester groups via combining the compound with 3 ml of TFA overnight, followed by methylation of vacuum concentrated residue with diazomethane. Following this, an excess of $CH_2N_2$, in ether, was added, in a solution of 90% MeOH. After stirring for a few minutes, excess $CH_2N_2$ was destroyed with acetic acid. The mixture was concentrated in vacuo, and residue was purified by flash chromatography (toluene/acetone: 10:1 plus 0.5% $Et_3N$), yielding compound 7, as a colorless oil (150 mg, 0.21 mmol, 81%). The total yield of compound "7," using three steps, was 32% $^1$H-NMR (250 $MH_2$ $CDCl_3$) data: $\delta$=2.78 (s, 6H, $((CH_2N)_3)$, 3.52 (s, 2H, 2-H), 3.59 (s, 12H, 6 $NCH_2CO_2$), 3.67 (s, 18H, 60 Me), 4.49 (s, 2H, $OCH_2Ar$), 7.47 (d, $^3$J=8.7 Hz, 2H, Ar), 8.21 (d, $^3$J=8.7

$H_2$, 2H, Ar). MALDI-MS, in positive mode, yielded: m/z: 701.6 [MH$^+$] calc.: 701.7, 722.6 [MNA$^+$] (calc.: 723.7), $C_{30}H_{44}N_4O_{15}*2H_2O$(736.0) Calc.: C 50.13, H 6.73, N 7.80. Found: C 50.17, H 6.39, N 7.68.

EXAMPLE 6

The final steps in the production of TAME-Hex A are described herein. A total of 70 mg, (0.10 mmol) of compound 7 was dissolved in MeOH (2 ml), and a solution of NaOH (160 mg, 4.0 mmol) in twice distilled water (1 ml) was added. After stirring for 24 hours, the mixture was acidified with HCl to a pH of about 1.5, and concentrated under reduced pressure. The solid residue was dissolved in a minimum amount of MeOH/$H_2O$ (1:3), loaded onto a RP-18 column and eluted with MeOH/$H_2O$ (1:3->1:1, +1% HOAc). Lyophilization of the collected and partially concentrated fractions yielded a fluffy, pale-yellow solid (51 mg, 0.08 mmol, 80%). $^1$H-NMR (250 MHz), $D_2O$: δ=3.36 (s, 6 H, C($CH_2N$)$_3$), 3.74 (s, 12 H, 6 $NCH_2CO_2$), 3.95 (s, 2 H, 2-H), 4.73 (s, 2 H, $OCH_2Ar$), 7.62 (d, $^3$J=8.2 Hz, 2 H, Ar, 8.26 (d, $^3$J=8.2 Hz, 2 H, Ar). MALDI-MS (positive mode) m/z: 639.5 [MNa]$^+$ (calc.: 639.5). $C_{24}H_{32}N_4O_{15}*H_2O$ (634.6): calc.: C 45.43, H 5.40, N 8.83, found: C 45.43, H 5.71, N 8.81.

Compound 8 (6.2 mg, 9.8 μmol) and sodium carbonate (4.3 mg, 40 μmol) were dissolved in 1.5 ml of water, and added to a suspension of Pd on charcoal (10%, 6 mg) in 1.5 ml of water, which had been previously stirred under a hydrogen atmosphere. After 4.5 hours of hydrogenation under slight pressure (balloon), the mixture was filtered through a pad of cellite (which was previously washed with water). Compound 8 will be referred to as "pre-TAME-HexA" hereafter, as it is a more stable form of compound 9, i.e., TAME-HexA. Both compounds 8 and 9 are chelators. Thiophosgene (5 μl, 25 μmol) in 3 ml of $CHCl_3$-layer was separated and the aqueous layer was partially evaporated in vacuo (30° C.) to remove any volatiles and lyophilized to compound 9 (9.8 mg), as an amorphous, nearly colorless solid. $^1$H-NMR (250 MHz, $D_2O$): aromatic proteins: δ=7.31-7.51 ppm (m, 2 H). MALDI-MS (positive mode, ATT-matrix) of a acidified (HCl) sample, m/z: 630.2 [MH]$^+$ (calc.: 629.5), 652.3 [MNa]$^+$ (calc.: 651.5).

EXAMPLE 7

This example, and the examples which follow, describe the synthesis of a second chelator, referred to as TAME-Hex B.

The teratosylate of pentaerythriol, described by Fleischer, et al., *J. Org. Chem.*, 36(20):3042-3044 (1971), incorporated by reference and shown as "10" in the figure, was used to make tetrakis-(amino methyl)-methane, described by Riemschneider, et al., *Monatsch. Chem.*, 1965:147-158. This is compound 11 in the figure. This compound, in turn, is reacted with four equivalents of benzaldehyde, followed by reduction of the aldimine, to form compound 12, the triazaadamantane, described by Fleischer, et al., *J. Org. Chem.*, 36(20):3042-3044 (1971). Compound 12 was used to make compound 13, i.e., 2-(amino methyl)-2-[(dibenzylamino)methyl]-propane-1,3-diamine tetrahydrochloride. This was done by stirring a solution of 12 (1.64 g, 3.37 mmol), and adding 1.22 ml.(7.0 mmol) DIPEA, and 0.7 ml (6.0 mmol) benzyl bromide, at room temperature. This mixture was stirred overnight, resulting in formation of a white suspension. The suspension was diluted, with 80 ml each of ether and toluene, and was then washed with 80 ml of brine & water. This resulted in an organic and aqueous layer. The organic layer was dried over $CaCl_2$, and concentrated under reduced pressure. Residue was suspended in ether, filtered, and washed with methanol. The yield was 1.66 g (2.88 mmol, 85%)k, of 7-[(dibenzylamino)methyl]-2,4,6-triphenyl-1,3,5-triazadamantane, as a white powder. The powder was dissolved in freshly distilled THF (40 ml), and 1.5 N HCl (50 ml), was added, with vigorous stirring, for 30 minutes. This removed the benzylidene protecting group. THF was removed by rotary evaporation, and the resulting aqueous solution was extracted with $CH_2Cl_2$ (twice, 50 ml each). The evaporation of the aqueous layer under reduced pressure yielded 1.27 g, 2.77 mmol, 96% yield, of compound 13 (77% yield relative to starting materials).

EXAMPLE 8

These experiments describe the manufacture of the hexamethyl ester of compound 13, i.e., tetramethyl 2-[bis(methoxycarbonyl methyl)amino]-2-[(dibenzylamino)methyl]-propylene-1,3-dinitrilotetraacetate.

A total of 1.25 g (2.53 mmol) of compound 13 was dissolved in 15 ml of dry DMF, which was then saturated with Ar. The mixture was then alkylated with 3.2 ml (21 mmol) of tert-butyl bromoacetate, and 2.8 g (26 mmol) $Na_2CO_3$, at 65° C., for 8 hours, followed by 12 hours of stirring at room temperature. The mixture was then diluted with 80 ml dichloromethane and 60 ml of water. This resulted in an organic layer and an aqueous layer. The organic layer was washed with 50 ml brine, dried over $Na_2SO_4$, concentrated, and subjected to flash chromatography with petroleum ether and ethyl acetate, in a 10:1 ratio. This resulted in the hexylated product as a colorless oil (1.12 g, 1.12 mmol, 44% yield), $R_f$=0.67, (petroleum ether/ethyl acetate: 4:1).

In order to improve the purification, the compound described supra was converted into its corresponding, hexa (methyl ester) by cleaving the tert butyl ester groups with TFA (10 ml) with which it was mixed, overnight, followed by vacuum concentrating the residue and methylating with diazomethane. Excess $CH_2N_2$, in ether solution was added to a solution of the reactant, in 90% MeOH. Following stirring, excess $CH_2N_2$ was destroyed with acetic acid. The mixture was then concentrated, in vacuo, and the residue was purified by flash chromatography (toluene/acetone: 10:1 plus 1% EtN). Compound 14 resulted, in a yield of 570 mg, 0.77 mmol, 70% as a colorless oil. The $^1$H-NMR data (250 MHz, $CDCl_3$) is as follows: δ-2.72 (s, 2H, 2-H), 2.90 (s, 6H, C($CH_2N$)$_3$), 3.59 (s, 16H, 6$NCH_2CO_2$, N($CH_2Ph$)$_2$), 3.65 (s, 18H, 60 Me), 7.27-7.34 (m, 10H, 2 Ph), $C_{37}H_{52}N_4O_{12}*H_2O$ (762.9). Calc.: 58.26, H 7.14, N 7.34. Found: C 58.32, H 7.03, N 7.25.

EXAMPLE 9

This example describes the final synthesis of TAME-HexB, or 2-[Bis(carboxymethylamino)methyl]-2-[(dibenzylamino)methyl]-propylene- 1,3-dinitrilotetraacetic acid, or compound 15 in the figure. A total of 350 mg (0.46 mmol), of compound 14 was dissolved in 5 ml of MeOH, and 6 ml of a solution of NaOH (480 mg, 12.0 mmol, in bidistilled water), was added. This was stirred, for 3 days, after which the mixture was acidified with HCl, to a pH of about 1. The solution was concentrated, under reduced pressure, and the resulting solid residue was dissolved in MeOH:$H_2O$, at a 1:4 ratio, which contained 1% of $Et_3N$. The solution was loaded onto an RP-18 column, and eluted with MeOH/$H_2O$ (1:4->10:1, plus 1% HOAc). Lyophilization followed, yielding a colorless solid (171 mg, 0.24 mmol, 52%), containing 1 eq each of HOAc and $Et_2N$. Crystallization of a portion of this product yielded compound 15, free of HOAc. The $^1$H-NMR data for the compound are as follows: (250 MHz, $D_2O$: A45*HOAc): δ −2.07 (s, 3H, OAc), 3.17 (br s, 6H $C(CH_2N_3)$), 3.41 (br s, 2H, 2-H), 3.54 (br s, 12H, $6NCH_2CO_2$), 4.40 (br s, 4H, $N(CH_2Ph)_2$), 7.53 (br s, 10H, 2 Ph). $^1$H-NMR (250 MHz, $D_2O$, Ph 12): 1.92 (s, 3H, OAc), 2.88 (br s, 2H, 2-H), 2.98 (br s, 6H, $C(CH_2N)_3$), 3.37 (br s, 12H, $6NCH_2CO_2$), 3.70 (br s, 4H, $N(CH_2Ph)_2$), 7.27-7.48 (m, 10H, 2 Ph) MALDI-MS (positive mode) m/z: 661.4 [MH]+ (calc.: 660.7), 683.5 [MNa+] (Calc.: 683.7). $C_{31}H_{40}N_4O_{12}$ (660.7): Calc.: C 56.36, H 6.10, N 8.48, Found: C 56.01, H 6.53, N 8.31.

EXAMPLE 10

The chelators defined by compounds 8 and 15 in FIG. 1 and as described, supra, were tested in transchelation experiments, using $^{111}In^{3+}$, and $^{67}Ga^{3+}$, using the known chelator DTPA as a competing ligand. Labelling was carried out using standard methods.

The results indicated that both chelators were labelled with both isotopes, and less than 0.1% radiometal remained unchelated. With respect to stability, both compounds 8 and 15, when labelled with $^{111}In$, showed that about 10% of the labelled material was intact after 24 hours.

FIGS. 2 and 3 show that the $^{67}Ga$ labelled chelators were even more stable. Labelled TAME-HexA was 94% intact after 10 days, and 99% of the labelled TAME-HexB was stable after the same period of time.

The foregoing data set forth aspects of the invention, which relate to compounds of formula:

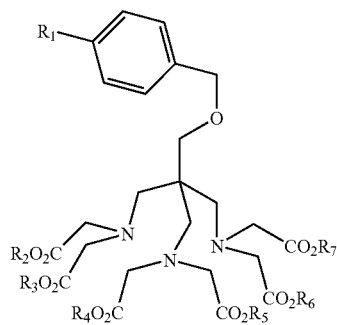

Wherein $R_1$ is a functional group, such as CN, SCN, $O_2N$, COOH, SH, a bromoacetamido group or another reactive group, and $R_2$ through $R_7$, which may be the same or different, are H, branched or straight chain alkyl moieties containing from 1 to 10, preferably 1 to 6 carbon atoms, which are preferably straight chained, and which may be substituted by O, N, S, a halide, or other moieties. In particularly preferred embodiments, $R_2$-$R_7$ are the same, and are H, or $C_1$-$C_6$ alkyl, and $R_1$ is $O_2N$ or SCN. Especially preferred are compounds where $R_1$ is $O_2N$, and $R_2$-$R_7$ are the same and are either Me or H, as well as compounds where $R_1$ is SCN, and $R_2$-$R_7$ are the same and are H.

A second group of compounds encompassed by the invention are compounds of formula:

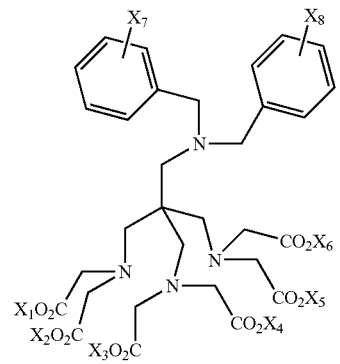

Wherein $X_1$-$X_6$ which may be the same or different, are H or straight chain or branched, substituted or unsubstituted $C_1$-$C_{10}$, preferably straight, unsubstituted, $C_1$-$C_6$ alkyl, $X_7$ and $X_8$, which may be the same or different, are H or a group as defined by $R^1$, supra, and Y is H or forms a C=O bond with the carbon atom. In especially preferred embodiments, $X_1$-$X_6$ are the same, and are either methyl or hydrogen.

The compounds of the invention are useful as chelators which can be used to form complexes with ions, such as metal ions. The ions can be detected with different kinds of techniques. The ions can be detected as they give rise to a detectable signal upon the application of some sort of external field or radiation, e.g. a magnetic field as in magnetic resonance imaging (MRI) or a external radiation field as in x-ray radiation, the chelate/ion complexes then act as contrasting agents. The ions can also be detected by various techniques if the ions are themselves sending out a detectable signal, e.g. if the ions are radioactive isotopes that send out gamma, beta or alpha radiation. Exemplary, but by no means the only types of radioactive ions with which the chelators can form complexes, are ions of gallium, $^{67}Ga^{3+}$ or $^{69}Ga^{3+}$, in particular.

The structure of the chelators permits their attachment to molecules, such as those listed supra, including antibodies, peptides, proteins, ligands, and so forth. The resulting complexes can be used therapeutically or diagnostically, as was elaborated upon supra. The complexes of chelator and target molecule, such as an antibody, is also a feature of this invention, as is the use of these complexes in therapeutic and diagnostic applications.

Also a feature of the invention are the intermediate compounds 2-13, described herein, as well as the processes for making these, as well as processes for making the compounds described supra.

Other features of the invention will be clear to the skilled artisan and need not be set forth herein.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A compound of formula

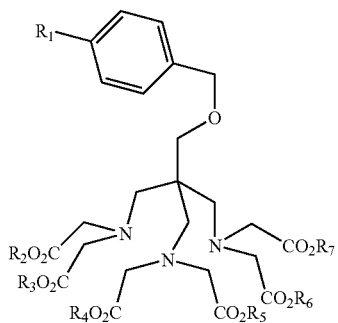

wherein $R_1$ is CN, SCN, $O_2N$, COOH, SH, or a bromoacetamido group, and $R_2$-$R_7$, which may be the same or different, are H, $C_1$-$C_{10}$ branched or straight chained, substituted or unsubstituted alkyl.

2. The compound of claim 1, wherein $R_2$-$R_7$ are the same.

3. The compound of claim 2, wherein $R_2$-$R_7$ are H.

4. The compound of claim 3, wherein $R_1$ is $O_2N$ or SCN.

5. The compound of claim 3, wherein $R_1$ is SCN.

6. The compound of claim 2, wherein $R_2$-$R_7$ are methyl.

7. The compound of claim 6, wherein $R_1$ is $O_2N$.

8. A chelation complex of a metal ion and the compound of claim 1.

9. A chelation complex of a metal ion and the compound of claim 5.

10. A chelation complex of a metal ion and the compound of claim 7.

11. The chelation complex of claim 8, 9, or 10, wherein said metal ion is a radioisotope.

12. The chelation complex of claim 11, wherein said radioisotope is $^{67}Ga^{3+}$.

* * * * *